United States Patent [19] [11] Patent Number: 4,723,052
Cochran [45] Date of Patent: Feb. 2, 1988

[54] POTATO VARIETY NAMED LC-1
[75] Inventor: John E. Cochran, Grandview, Wash.
[73] Assignees: S. Lynn Loosli; Curtis A. Loosli, both of Fremont, Id. ; a part interest to each
[21] Appl. No.: 874,161
[22] Filed: Jun. 13, 1986
[51] Int. Cl.⁴ ............................................. A01H 5/00
[52] U.S. Cl. ......................................... 800/1; Plt./89
[58] Field of Search ............................. Plt./89; 800/1

Primary Examiner—Robert E. Bagwill
Attorney, Agent, or Firm—M. Reid Russell

[57] ABSTRACT

The new potato variety is classified as having no known parentage. It was discovered in a cultivated field of Butte variety potatoes near Ashton, Id. The new variety produces tubers that mature early and are suitable for fresh market use having high solids, low sugars, a fine mealy texture, good processing quality and good storability. The variety is resistant to metribuzin herbicide injury, leafroll net necrosis, veinal necrosis, jelly or sugar ends, second growths, growth cracking and black spot or shatter bruising. Its tubers are oblong to long, with shallow eyes, a smooth skin of moderate thickness, and exhibits moderate russeting. The tubers rarely express hollow heart, internal brown spot or other defects, and seldom develop storage rots. LC-1 is susceptible to most soilborne, foilage, and viral diseases, but is resistant to scab and seldom develops blackleg. The variety is well adapted to the sandy soils of the Western United States.

3 Claims, 4 Drawing Figures

POTATO VARIETY NAMED LC-1

SUMMARY OF THE INVENTION

The present invention relates to a new and distinct variety of potato which was discovered by me growing as a small, white flowered aberrant plant in a field of the Butte variety. Butte has a large plant and purple flowers. The new potato variety was found in 1978 growing in a potato field near Ashton, Idaho on a farm owned by Curtis Loosli and has since been identified as (78-LC-1), hereinafter referred to as LC-1. Seed for planting the Butte variety was originally obtained from the Idaho State Seed Farm at Tetonia, Idaho.

Breeders and seedsmen who have seen this potato do not recognize this selection as anything that they have previously selected or evaluated. The potato variety has therefore been classified as a field selection with no known parentage. Selection and initial evaluation was done on Loosli Farms and in a greenhouse located near Ashton, Idaho. Further evaluations were done at the Aberdeen, Idaho Research and Extension Center of the University of Idaho and at the Washington State University Irrigated Agriculture Research and Extension Center, Prosser, Wash. Testing in the western region variety trials in 1982 and commercial trials were initiated in 1984.

LC-1 plants are upright and bushy and very small to medium small compared to the Butte variety planted in the field where this variety was found. The stems are maroon-purple mottled, which coloring is more predominant on older portions of the stem, starting at the leaf nodes and fading downwardly towards the next lower node. The plant leaves are small to medium small, green to dark green and are moderately open when young and recurve from maturity to senescence. This variety has flowers with off-white to yellow buds that are numerous as compared to most potato varieties, such as Russet Burbank. The flowers are male and female fertile and when open and pollinated have numerous seed balls that are full of seed.

LC-1 is resistant to metribuzin herbicide injury, leafroll net necrosis, jelly or sugar ends, second growths, growth cracking and black spot and shatter bruising. LC-1 is susceptible to most pests, soilborne, foliage, and viral diseases, but is resistant to scab, seldom has blackleg and usually does not die as early as Norgold Russet. It is only moderately susceptible to mosaic viruses X and Y, leafroll virus, Verticillium wilt and Colorado potato beetle. This new variety seems particularly well adapted to sandy soils in the Western United States. However, it has also performed well in Maine and other areas on heavier soils.

LC-1 tubers are oblong to long and smooth, with an average of 5.3 tubers per plant. Under stress conditions tubers will have pear shapes. The tuber eyes are shallow, well distributed, and sprouts are white with purple spreading from the base. The tubers have few external blemishes and skin of moderate thickness, uniform texture and moderate russeting. LC-1 is a high quality variety, intended primarily for early fresh market use. However, it has moderately high solids and low sugars and its processing quality and storability are acceptable.

Comparison yields over a four-year test period were lower than Russet Burbank but equal or greater than Norgold Russet. Yields of LC-1 were relatively lower in single row trials where its small plants were overgrown by adjacent large-vined varieties. LC-1 has a large incidence of pear-shaped tubers in such tests.

LC-1 has consistently less internal blemishes than either Russet Burbank or Norgold Russet. It rarely expresses hollow heart, internal brown spot, brown center, stem end browning, net necrosis, or other internal defects.

The storage qualities of LC-1 tubers was measured on material taken from variety trials over a four-year period, 1982-1985, and on larger samples grown for certified seed production. Shrinkage and weight loss for LC-1 was less than Russet Burbank and Norgold Russet. LC-1 seldom had storage rots and consistently stored better than Norgold Russet in every regard. Samples for each of the four years were evaluated for bruising, with LC-1 bruising equal to or less than Russet Burbank and Norgold Russet.

When evaluated for cooking qualities, LC-1 tubers consistently rated higher than those of Norgold Russet in both specific gravity and processing quality. LC-1 tubers bake well, have a fine mealy texture and are excellent as mashed potatoes or french fries. Fry color is generally as good as Russet Burbank. The flesh is white and has a delicate flavor somewhat resembling Norgold Russet.

LC-1 has been propagated asexually over a number of years, the asexual propagation involving cutting the tuber into segments, each containing an eye for planting. This propagation has demonstrated that the unique characteristics of this new variety wil be reproduced true to form and are established and transmitted through succeeding propagations.

BRIEF DESCRIPTION OF THE PHOTOGRAPHS

DETAILED DESCRIPTION

Figure 1:
FIG. 1 shows, in color, as true as is reasonably possible, a plant of a new variety of potato identified as LC-1 as it was discovered on a farm near Ashton, Idaho growing amongst the Butte variety.

The following is a detailed description of my new variety of potato identified as LC-1. Color terminology shown herein is to be accorded its ordinary dictionary significance except where otherwise indicated. The tubers described were grown at Ashton, Idaho and harvested in October of each respective year from 1979 to 1982.

Plant: Very small to medium small, upright and bushy as compared with Russet Burbank.
  Stems: Maroon-purple mottling most prominent on older portions of stem starting at leaf nodes and fading downwardly towards next lower node.
  Wings: Medium size, reaching outwardly ½ to ¾ of the distance to the next node.
  Nodes: Not prominent.
  Leaves: Generally small to medium small compared to Russet Burbank and other potato varieties; color green to dark green; moderately pubescent, moderately open when young, and recurved from maturity to senescence.

Terminal Leaflets: Ovate, apex acuminate, base slightly lobed, slightly asymmetrical, means blade length—66 mm, mean blade width 64 mm, index 96.

Primary Leaflets: Ovate, apex acuminate, slightly asymmetric, three (3) to four (4) pairs, mean blade length 59 mm, mean width 54 mm, index 92.

Secondary Leaflets: Moderate.

Tertiary Leaflets; Moderate.

Midribs and Petioles: Light green as compared with Russet Burbank, sparse pigmentation, moderate pubescence.

Flowers: Moderately numerous as compared with Russet Burbank.

Buds: Off-white, ochroleucrous, to pale yellow.

Calyx: Shape-rotate with elongated mucronate tip, light green, mean length 6 mm; moderate pubescence.

Corolla: White, medium size, shape is rotate recurved with slightly arcuate tip.

Anthers: Yellow. Male and female fertile. Produces numerous open fertile seed balls, each full of seed.

*Tubers:* Oblong to long, often pear shaped. Mean length for sample of twenty (20) 227 gram to 284 gram tubers of 111 mm; with a mean width of 57 mm; and a mean thickness of 73 mm.

Indices: width to length 51, thickness to length 66, thickness to width 78. Average number of tubers per plant=5.3.

Skin: Smooth, medium brown, russeted of average thickness.

Eyes: Shallow, well distributed. Mean number on 255 gram tuber=twelve (12).

Flesh: White.

Sprouts: White with purple at base, spreading to white.

Maturity: Very early. Can be harvested in late July and early August in Northern growing areas.

Characteristics: Consistently free of external blemishes such as growth cracks, rough skin, second growths, dumbbell shapes and other malformations. Tubers seldom have internal blemishes such as hollow heart, brown center, internal brown spot, heat necrosis, stem end browning, sugar ends or net necrosis. LC-1 is resistant to scab.

Uses: To be used primarily as an early fresh market variety in the same class as Norgold Russet but can be stored and processed like Russet Burbank. Tubers bake well with a fine mealy texture. They make excellent mashed potatoes and french fries and have a mild delicate flavor resembling that of Norgold Russet. LC-1 consistently rates higher than Norgold Russet in specific gravity and processing quality.

Yields: Over a four-year test period, total yields of the LC-1 were lower than Russet Burbank, but were equal or greater than Norgold Russet. Yields of U.S. Nr. 1 tubers usually better than either of these two standard varieties. Number of tubers per plant were relatively low with the averages ranging from 3.9 to 6.7 tubers per plant. In single row trials, where small plants of LC-1 were overgrown by adjacent large-vined varieties, there was a high incidence of pear-shaped tubers.

Storage: LC-1 tubers have less weight loss in storage than Russet Burbank and Norgold Russet and consistently store better than Norgold Russet. In several trials LC-1 tubers expressed good storage rot resistance.

Disease Evaluation:

Except for its resistance to scab and storage rots, LC-1 is apparently susceptible to most diseases and pests. However, it is only moderately susceptible to diseases encountered in growing areas of the Northwestern United States. It has so far expressed very little blackleg.

TABLES

Hereinbelow are included Tables I, II, III and IV, that detail LC-1 characteristics for, respectively: plant and tuber characteristics of plantings in 1981–1985; disease characteristics of plantings in 1981–1985; tuber internal characteristics of plantings in 1981–1985; and yield and grade characteristics of plantings in 1982–1984 in Washington and Oregon. The tables are self-explanatory, each including a scale that is defined below that table.

TABLE I

| Plant and Tuber Characteristics 1981–1985 | | | | | |
| --- | --- | --- | --- | --- | --- |
| Flower Color | 1.0 | White | Yield Rating | 2.9 | Medium 350–500 cwt/A |
| Seed Ball Production | 2.5 | Average | % # 1's | 3.4 | Medium 70–80% |
| Determinate | 4.4 | Small to medium small | Tuber size | 3.6 | Medium 7–8 oz avg. |
| Shape-Tuber | 4.0 | Oblong-long | Uniformity-Tuber | 3.2 | Average |
| Skin-Tuber | 3.7 | Medium Russet | Overall Rating | 3.7 | Above avg. |
| Specific Gravity | 2.5 | Medium 1.075–1.080 | Metribuzin | 4.8 | Resistant |

Scale 1 = poor, least, short
5 = good, most, long

TABLE II

| Disease Characteristics 1981–1985 | | | | | |
| --- | --- | --- | --- | --- | --- |
| Early Blight | 3.7 | Moderate Resistance | Rot (Soft Rot) | 4.5 | Very Resistant |
| Early Dying | 1.7 | Susceptible | Mosaic (Severe-Y) | 3.2 | Moderately Susceptible |
| Verticillium | 2.1 | Susceptible | Leaf roll | 3.7 | Moderately Susceptible |
| Sclerotinia | 1.1 | Very Susceptible | Nematode (Root Knot) | 2.3 | Susceptible |
| Scab | 4.2 | Resistant | Colorado Potato Beetle | 2.5 | Moderately Susceptible |

Scale 1 = Severe Disease Symptoms
5 = No Disease Symptoms

TABLE III

| Tuber Internal Characteristics 1981–1985 | | | |
| --- | --- | --- | --- |
| Malformation | 4.3 | Hollow Heart & Brown Center | 4.9 |
| Knobs | 4.8 | Internal Brown Spot | 5.0 |
| Flat | 4.2 | Shatter Bruise | 4.8 |
| Pear | 2.8 | Shrivel (Storage) | 4.1 |
| Elephant | 4.9 | Black Spot | 4.8 |
| Cracking | 4.9 | Sprouting | 3.0 |

Scale 1 = Severe Symptom
5 = No Symptom

TABLE IV

Yield and Grade Characteristics 1982–1984
Washington and Oregon

| Year | CWT/A Total | % # 1's | % # 2's | Specific G. | Wt In oz Tuber | # Tuber/ Hill |
|---|---|---|---|---|---|---|
| 1982 | 461 | | | | | |
| 1982 | 244 | 60.3 | | 1.070 | | |
| 1983 | 692 | 82.0 | | 1.078 | | |
| 1983 | 402 | 76.0 | | 1.077 | | |
| 1983 | 454 | 84.0 | | 1.082 | | |
| 1984 | 430 | 81.4 | 0 | 1.082 | 7.3 | 3.9 |
| 1984 | 611 | 73.9 | 8.2 | 1.074 | 6.2 | 6.7 |
| 1984 | 673 | 94.7 | 0 | 1.075 | 8.9 | 5.9 |
| 1984 | 657 | 93.4 | 0.2 | 1.073 | 10.4 | 5.4 |
| 1984 | 355 | 85.6 | 0 | 1.071 | 6.0 | 4.7 |
| 1984 | 364 | 79.7 | 1.2 | 1.076 | | |
| Avg. | 486 | 81.1 | 1.6 | 1.076 | 7.76 | 5.32 |

I claim:

1. A new and distinct variety of potato named LC-1 that has been classified as having no known parentage substantially as shown and described and characterized, compared to the variety Russet Burbank as (a) a plant that is very small to medium small, upright and bushy having small to medium small green to dark green leaves with stems showing maroon-purple mottling; (b) having numerous white male and female fertile flowers with yellow anthers; and (c) producing on the average 5 to 6 tubers per plant early in the season that are oblong to long, smooth, shallow-eyed, medium-netted and russeted of hiqh quality suitable for market use, having high solids and low sugar, which tuber is disease resistant, rarely expresses hollow heart or other internal defects, seldom develops storage rots, and is particularly well adapted to sandy soils of the Western United States.

2. Tubers of the variety of claim 1.

3. Propagating material of the variety of claim 1.

* * * * *

UNITED STATES PATENT AND TRADEMARK OFFICE
CERTIFICATE OF CORRECTION

PATENT NO. : 4,723,052

DATED : February 2, 1988

INVENTOR(S) : John E. Cochran

Figure 2:
FIG. 2 shows, in color, as true as is reasonably possible, flower buds of LC-1.
Figure 3:
FIG. 3 shows, in color, as true as is reasonably possible, typical blooming flowers and buds of LC-1.
Figure 4:
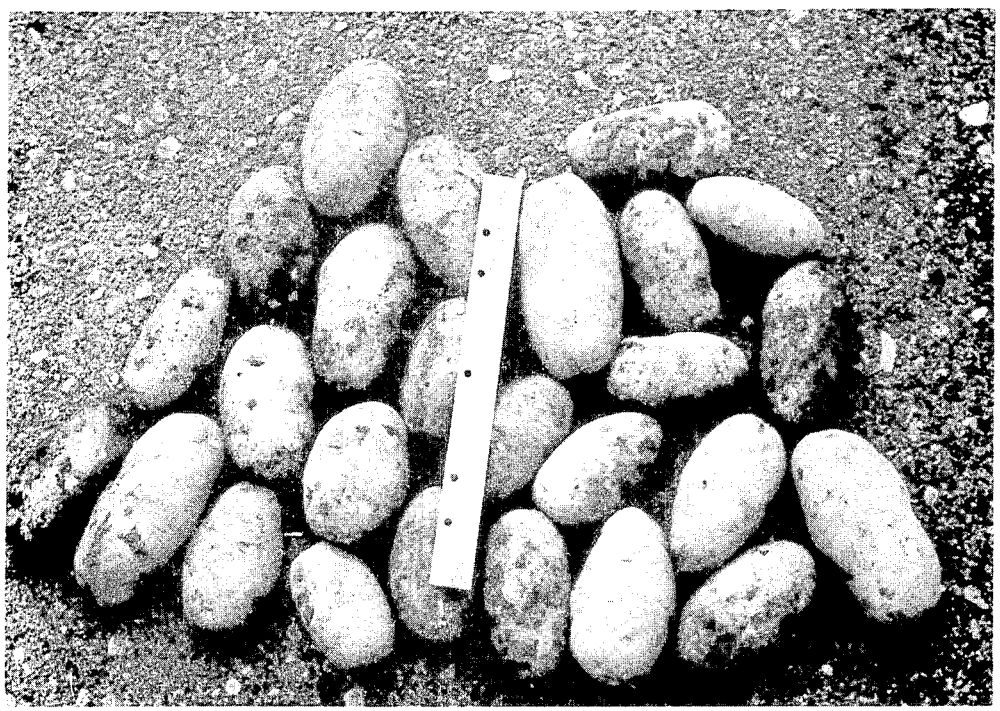
FIG. 4 shows, in color, as true as is reasonably possible, tubers of LC-1 grown in Ashton, Idaho, including a twelve inch ruler for dimensional comparison and shows the surface appearance of LC-1 at harvest.
Figure 1:
Figure 2:

It is certified that error appears in the above-identified patent and that said Letters Patent is hereby corrected as shown below:

The sheet of drawing consisting of FIGS. 1 and 2, should appear as shown on the attached sheet.

Signed and Sealed this

Seventeenth Day of January, 1989

Attest:

DONALD J. QUIGG

Attesting Officer

Commissioner of Patents and Trademarks